United States Patent
Carreira

(10) Patent No.: US 8,044,224 B2
(45) Date of Patent: Oct. 25, 2011

(54) CHIRAL IRIDIUM AQUA COMPLEX AND METHOD FOR PRODUCING OPTICALLY ACTIVE HYDROXY COMPOUND BY USING THE SAME

(75) Inventor: Erick M. Carreira, Zurich (CH)

(73) Assignees: Sumitomo Chemical Company, Limited, Tokyo (JP); Erick M. Carreira, Zurich (CH)

( * ) Notice: Subject to any disclaimer, the term of this patent is extended or adjusted under 35 U.S.C. 154(b) by 203 days.

(21) Appl. No.: 12/524,632

(22) PCT Filed: Jan. 29, 2008

(86) PCT No.: PCT/JP2008/051287
§ 371 (c)(1),
(2), (4) Date: Jul. 27, 2009

(87) PCT Pub. No.: WO2008/093668
PCT Pub. Date: Aug. 7, 2008

(65) Prior Publication Data
US 2010/0016618 A1    Jan. 21, 2010

(30) Foreign Application Priority Data
Jan. 29, 2007   (JP) .................................. 2007-017670

(51) Int. Cl.
*C07F 15/00* (2006.01)
*C07C 255/00* (2006.01)
(52) U.S. Cl. ......................... 556/137; 558/426; 558/488
(58) Field of Classification Search .................. 558/426, 558/488; 556/137
See application file for complete search history.

(56) References Cited

FOREIGN PATENT DOCUMENTS

| EP | 1 932 824 A1 | 6/2008 |
| JP | 11-335385 A | 12/1999 |
| JP | 2003-286294 A | 10/2003 |
| WO | WO 2007/032409 A1 | 3/2007 |

OTHER PUBLICATIONS

Abura et al., *J. Am. Chem. Soc.*, 125(14): 4149-4154 (2003).
Fujii et al., *J. Am. Chem. Soc.*, 118(10): 2521-2522 (1996).
Li et al., *Synlett*, 8:1155-1160 (2006).
McFarland et al., *J. Am. Chem. Soc.*, 127(39): 13490-13491 (2005).
Ogo et al., *Organometallics*, 18(26): 5470-5474 (1999).
Ogo et al., *Organometallics*, 20(23): 4903-4910 (2001).
Ogo et al., *J. Am. Chem. Soc.*, 126(10): 3020-3021 (2004).
Poth et al., *Eur. J. Inorg. Chem.*, 5: 1361-1369 (2001).
Wang et al., *J. Org. Chem.*, 70(23): 9424-9429 (2005).
Wu et al., *Chem. Commun.*, 4447-4449 (2005).

*Primary Examiner* — Porfirio Nazario Gonzalez
(74) *Attorney, Agent, or Firm* — Leydig, Voit & Mayer, Ltd.

(57) ABSTRACT

The invention relates to a chiral iridium aqua complex of formula (1):

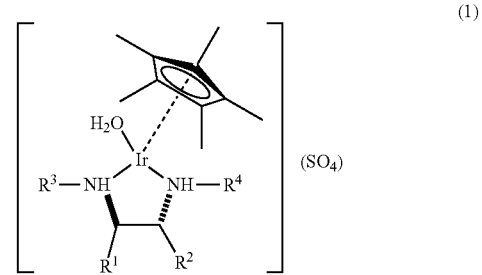

(1)

wherein $R^1$ and $R^2$ are the same or different and each is an aryl group optionally having at least one substituent selected from the group consisting of a halogen atom, an alkyl group having 1 to 6 carbon atoms, an alkoxy group having 1 to 6 carbon atoms, a haloalkoxy group having 1 to 6 carbon atoms, a nitro group, a carboxyl group and a cyano group, or the like; and wherein $R^3$ and $R^4$ are the same or different and each is an alkyl group or the like, as well as the use of such a chiral iridium aqua complex for asymmetric transfer hydrogenation.

13 Claims, No Drawings

CHIRAL IRIDIUM AQUA COMPLEX AND METHOD FOR PRODUCING OPTICALLY ACTIVE HYDROXY COMPOUND BY USING THE SAME

TECHNICAL FIELD

The present invention relates to a novel chiral iridium aqua complex, a production method thereof and a production method of an optically active hydroxy compound, which comprises asymmetric transfer hydrogenation using the complex.

BACKGROUND ART

As a production method of an optically active hydroxy compound from a carbonyl compound by asymmetric transfer hydrogenation using an iridium complex, J. Am. Chem. Soc. 2004, 126, 3020-3021 discloses a method using an iridium aqua complex represented by

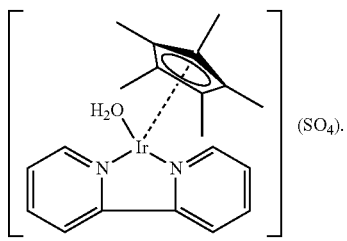

In addition, Eur. J. Inorg. Chem. 2001, 1361-1369 discloses a chiral iridium aqua complex having perchlorate ion.

DISCLOSURE OF THE INVENTION

The present inventors have conducted intensive studies to develop a novel chiral iridium complex that can be used for a production method of an optically active hydroxy compound by asymmetric transfer hydrogenation, and completed the present invention.

Accordingly, the present invention provides

<1> a chiral iridium aqua complex represented by the formula (1):

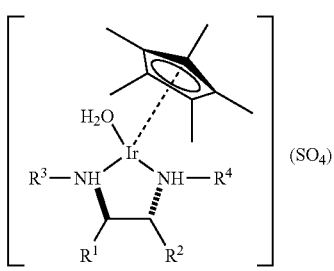

wherein
$R^1$ and $R^2$ are the same or different and each is an aryl group optionally having at least one substituent selected from the group consisting of a halogen atom, an alkyl group having 1 to 6 carbon atoms, an alkoxy group having 1 to 6 carbon atoms, a haloalkoxy group having 1 to 6 carbon atoms, a nitro group, a carboxyl group and a cyano group, or $R^1$ and $R^2$ in combination show a straight chain alkylene group having 3 or 4 carbon atoms to form a ring together with the carbon atoms they are bonded to, wherein the straight chain alkylene group having 3 or 4 carbon atoms optionally has alkyl group(s) having 1 to 6 carbon atoms or alkoxy group(s) having 1 to 6 carbon atoms, and $R^3$ and $R^4$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom;

<2> the complex of <1>, wherein the aryl group is a phenyl group;

<3> the complex of <1> or <2>, wherein $R^3$ and $R^4$ are the same or different and each is an alkyl group having 1 to 10 carbon atoms or a hydrogen atom;

<4> the complex of <1>, wherein the chiral iridium aqua complex represented by the formula (1) is a complex represented by the formula (2):

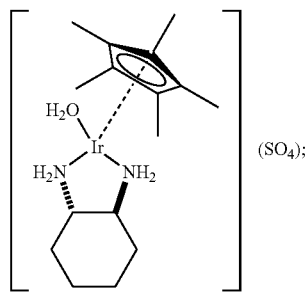

<5> the complex of <1>, wherein the chiral iridium aqua complex represented by the formula (1) is a complex represented by the formula (2-S):

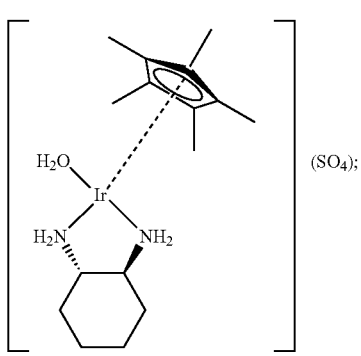

<6> the complex of <1>, wherein the chiral iridium aqua complex represented by the formula (1) is a complex represented by the formula (3):

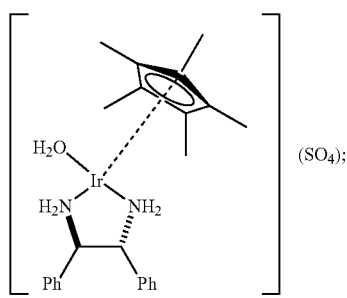

(3)

<7> the complex of <1>, wherein the chiral iridium aqua complex represented by the formula (1) is a complex represented by the formula (3-R):

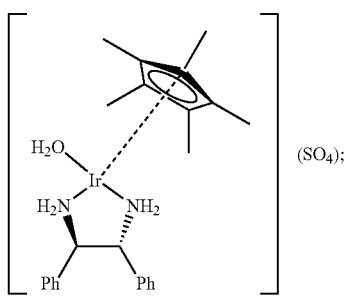

(3-R)

<8> the complex of <1>, wherein the chiral iridium aqua complex represented by the formula (1) is a complex represented by the formula (4):

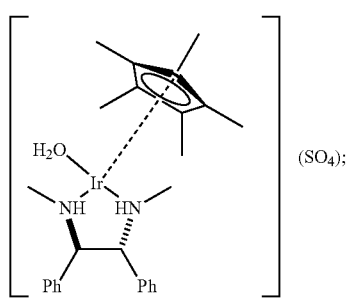

(4)

<9> the complex of <1>, wherein the chiral iridium aqua complex represented by the formula (1) is a complex represented by the formula (4-R):

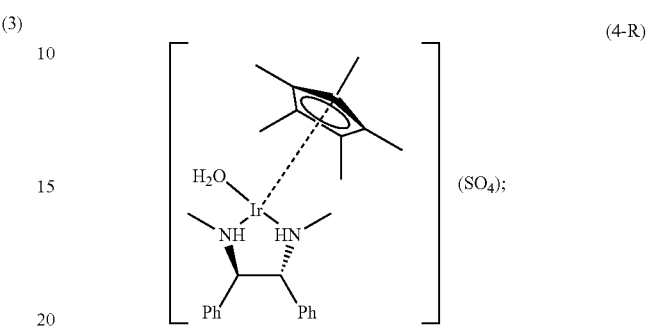

<10> a method of producing a chiral iridium aqua complex represented by the formula (1):

(1)

wherein $R^1$ and $R^2$ are the same or different and each is an aryl group optionally having at least one substituent selected from the group consisting of a halogen atom, an alkyl group having 1 to 6 carbon atoms, an alkoxy group having 1 to 6 carbon atoms, a haloalkoxy group having 1 to 6 carbon atoms, a nitro group, a carboxyl group and a cyano group, or $R^1$ and $R^2$ in combination show a straight chain alkylene group having 3 or 4 carbon atoms to form a ring together with the carbon atoms they are bonded to, wherein the straight chain alkylene group having 3 or 4 carbon atoms optionally has alkyl group(s) having 1 to 6 carbon atoms or alkoxy group(s) having 1 to 6 carbon atoms, and $R^3$ and $R^4$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, which comprises reacting an iridium complex represented by the formula (8):

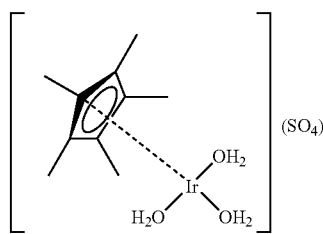

with a chiral diamine represented by the formula (9):

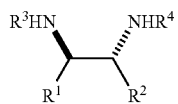

wherein $R^1$, $R^2$, $R^3$ and $R^4$ are as defined above;

<11> a chiral iridium aqua complex represented by the formula (5):

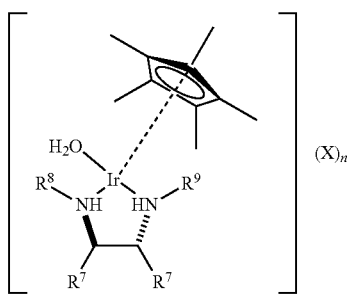

wherein $R^7$ is an aryl group substituted by haloalkyl group(s) having 1 to 6 carbon atoms, $R^8$ and $R^9$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, X is a monovalent or divalent anion, and n is 2 when X is a monovalent anion, or n is 1 when X is a divalent anion;

<12> the complex of <11>, wherein the chiral iridium aqua complex represented by the formula (5) is a complex represented by the formula (5-R):

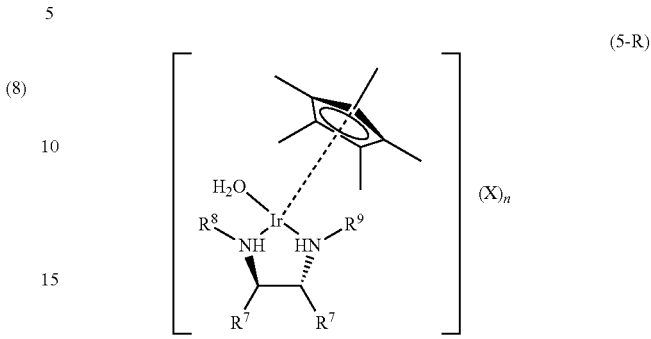

wherein $R^7$, $R^8$, $R^9$, X and n are as defined in <11>;

<13> the complex of <11> or <12>, wherein the aryl group substituted by haloalkyl group(s) having 1 to 6 carbon atoms is a phenyl group substituted by trifluoromethyl group(s);

<14> the complex of <13>, wherein the phenyl group substituted by trifluoromethyl group(s) is a 3-trifluoromethylphenyl group;

<15> the complex of any of <11> to <14>, wherein $R^8$ and $R^9$ are the same or different and each is a hydrogen atom or an alkyl group having 1 to 10 carbon atoms;

<16> the complex of any of <11> to <15>, wherein X is a chloride ion, a bromide ion, an iodide ion, a methanesulfonate ion, a trifluoromethanesulfonate ion, a formate ion, an acetate ion, a trichloroacetate ion, a nitrate ion, a sulfate ion, an acetylacetonate ion, a hexafluorophosphate ion or a tetrafluoroborate ion;

<17> the complex of any of <11> to <15>, wherein X is a sulfate ion;

<18> A method of producing a chiral iridium aqua complex represented by the formula (5):

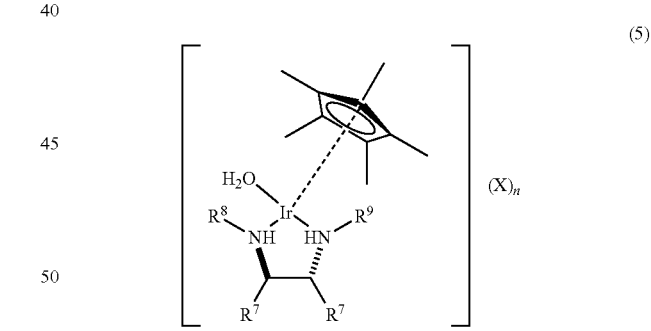

wherein $R^7$ is an aryl group substituted by haloalkyl group(s) having 1 to 6 carbon atoms, $R^8$ and $R^9$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, X is a monovalent or divalent anion, and n is 2 when X is a monovalent anion, or n is 1 when X is a divalent anion, which comprises reacting an iridium complex represented by the formula (10):

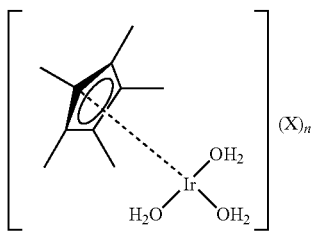

(10)

wherein X and n are as defined above,
with a chiral diamine represented by the formula (11):

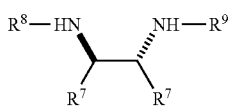

(11)

wherein $R^7$, $R^8$ and $R^9$ are as defined above;
<19> a method of producing an optically active hydroxy compound represented by the formula (7):

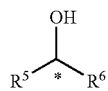

(7)

wherein
$R^5$ is an aryl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; a heteroaryl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; a cycloalkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; or an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group,
$R^6$ is a carbamoyl group optionally substituted by one or two alkyl groups having 1 to 6 carbon atoms wherein the two alkyl groups having 1 to 6 carbon atoms in combination optionally form a ring containing the nitrogen atom, and the methylene group of the ring is optionally replaced by an oxygen atom; an alkyl group optionally having at least one substituent selected from the group consisting of a halogen atom, an alkoxy group having 1 to 6 carbon atoms, a haloalkoxy group having 1 to 6 carbon atoms, a nitro group, a carboxyl group and a cyano group; or a carboxyl group, and
the carbon atom marked with * is an asymmetric carbon atom, which comprises subjecting a carbonyl compound represented by the formula (6):

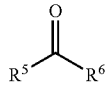

(6)

wherein $R^5$ and $R^6$ are as defined above,
to asymmetric transfer hydrogenation in the presence of a chiral iridium aqua complex represented by the formula (1):

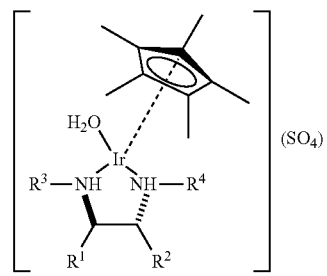

(1)

wherein
$R^1$ and $R^2$ are the same or different and each is an aryl group optionally having at least one substituent selected from the group consisting of a halogen atom, an alkyl group having 1 to 6 carbon atoms, an alkoxy group having 1 to 6 carbon atoms, a haloalkoxy group having 1 to 6 carbon atoms, a nitro group, a carboxyl group and a cyano group, or
$R^1$ and $R^2$ in combination show a straight chain alkylene group having 3 or 4 carbon atoms to form a ring together with the carbon atoms they are bonded to, wherein the straight chain alkylene group having 3 or 4 carbon atoms optionally has alkyl group(s) having 1 to 6 carbon atoms or alkoxy group(s) having 1 to 6 carbon atoms, and
$R^3$ and $R^4$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, or
a chiral iridium aqua complex represented by the formula (5):

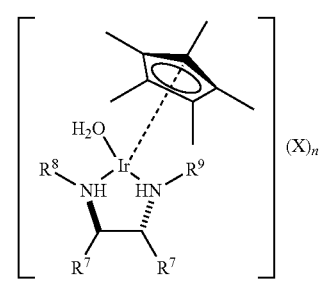

(5)

wherein
$R^7$ is an aryl group substituted by haloalkyl group(s) having 1 to 6 carbon atoms, $R^3$ and $R^9$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, X is a monovalent or divalent anion, and n is 2 when X is a monovalent anion, or n is 1 when X is a divalent anion;

<20> the method of <19>, wherein the asymmetric transfer hydrogenation is carried out in the presence of formic acid or a salt thereof;

<21> the method of <19>, wherein the asymmetric transfer hydrogenation is carried out in the presence of formic acid;

<22> the method of <19>, <20> or <21>, wherein the asymmetric transfer hydrogenation is carried in water or in a mixed solvent of water and an alcohol solvent;

<23> the method of any of <19> to <22>, wherein $R^6$ is a carboxyl group, a carboxymethyl group, a cyanomethyl group or a nitromethyl group;

<24> use of a chiral iridium aqua complex represented by the formula (1):

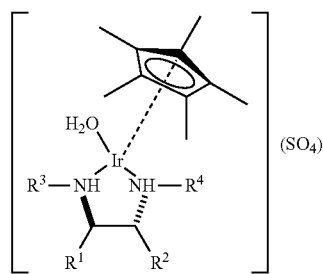

(1)

wherein $R^1$ and $R^2$ are the same or different and each is an aryl group optionally having at least one substituent selected from the group consisting of a halogen atom, an alkyl group having 1 to 6 carbon atoms, an alkoxy group having 1 to 6 carbon atoms, a haloalkoxy group having 1 to 6 carbon atoms, a nitro group, a carboxyl group and a cyano group, or $R^1$ and $R^2$ in combination show a straight chain alkylene group having 3 or 4 carbon atoms to form a ring together with the carbon atoms they are bonded to, wherein the straight chain alkylene group having 3 or 4 carbon atoms optionally has alkyl group(s) having 1 to 6 carbon atoms or alkoxy group(s) having 1 to 6 carbon atoms, and $R^3$ and $R^4$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, or a chiral iridium aqua complex represented by the formula (5):

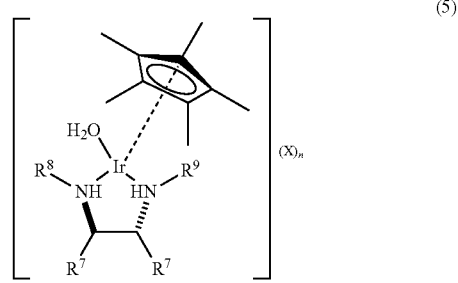

(5)

wherein $R^7$ is an aryl group substituted by haloalkyl group(s) having 1 to 6 carbon atoms, and $R^8$ and $R^9$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, X is a monovalent or divalent anion, n is 2 when X is a monovalent anion, or n is 1 when X is a divalent anion, for asymmetric transfer hydrogenation of a carbonyl compound represented by the formula (6):

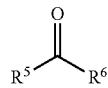

(6)

wherein $R^5$ is an aryl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; a heteroaryl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; a cycloalkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; or an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, and $R^6$ is a carbamoyl group optionally substituted by one or two alkyl groups having 1 to 6 carbon atoms wherein the two alkyl groups having 1 to 6 carbon atoms in combination optionally form a ring containing the nitrogen atom, and the methylene group of the ring is optionally replaced by an oxygen atom; an alkyl group optionally having at least one substituent selected from the group consisting of a halogen atom, an alkoxy group having 1 to 6 carbon atoms, a haloalkoxy group having 1 to 6 carbon atoms, a nitro group, a carboxyl group and a cyano group; or a carboxyl group;
and the like.

The chiral iridium aqua complex represented by the formula (1) or the formula (5) of the present invention is novel, and an optically active hydroxy compound can be produced by asymmetric transfer hydrogenation using the complex.

BEST MODE FOR CARRYING OUT THE INVENTION

First, a chiral iridium aqua complex represented by the formula (1):

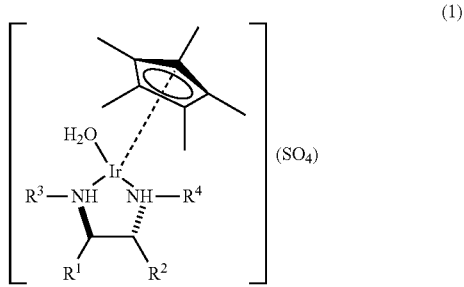

(1)

wherein
$R^1$ and $R^2$ are the same or different and each is an aryl group optionally having at least one substituent selected from the group consisting of a halogen atom, an alkyl group having 1 to 6 carbon atoms, an alkoxy group having 1 to 6 carbon atoms, a haloalkoxy group having 1 to 6 carbon atoms, a nitro group, a carboxyl group and a cyano group, or
$R^1$ and $R^2$ in combination show a straight chain alkylene group having 3 or 4 carbon atoms to form a ring together with the carbon atoms they are bonded to, wherein the straight chain alkylene group having 3 or 4 carbon atoms optionally has alkyl group(s) having 1 to 6 carbon atoms or alkoxy group(s) having 1 to 6 carbon atoms, and
$R^3$ and $R^4$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom (hereinafter to be abbreviated as complex (1)) is explained.

In the formula of complex (1), examples of the aryl group for $R^1$ or $R^2$ include an aryl group having 6 to 14 carbon atoms. Of these, a phenyl group, a naphthyl group, an anthryl group, a phenanthryl group, an acenaphthyl group, a biphenylyl group and the like are preferable, and a phenyl group is more preferable.

Examples of the halogen atom for $R^1$ or $R^2$ include a fluorine atom, a chlorine atom, a bromine atom and an iodine atom.

The alkyl group having 1 to 6 carbon atoms for $R^1$ or $R^2$ may be straight chain or branched chain, and examples thereof include a methyl group, an ethyl group, a propyl group, an isopropyl group, a butyl group, an isobutyl group, a sec-butyl group, a tert-butyl group, a pentyl group, an isopentyl group, a neopentyl group, a hexyl group and the like.

The alkoxy group having 1 to 6 carbon atoms for $R^1$ or $R^2$ may be straight chain or branched chain, and examples thereof include a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a hexyloxy group and the like.

The haloalkoxy group having 1 to 6 carbon atoms for $R^1$ or $R^2$ may be straight chain or branched chain, and examples thereof include a fluoromethoxy group, a difluoromethoxy group, a trifluoromethoxy group, a 2-fluoroethoxy group, a 2,2-difluoroethoxy group, a 2,2,2-trifluoroethoxy group, a 3-fluoropropoxy group, a 4-fluorobutoxy group, a 5-fluoropentyloxy group, a 6-fluorohexyloxy group and the like.

Examples of the straight chain alkylene group having 3 or 4 carbon atoms such that $R^1$ and $R^2$ in combination form a ring together with the carbon atoms they are bonded to include a trimethylene group and a tetramethylene group. The alkyl group having 1 to 6 carbon atoms and alkoxy group having 1 to 6 carbon atoms which the straight chain alkylene group having 3 or 4 carbon atoms optionally has are the same as the above-mentioned groups. Specific examples of the formed ring include a cyclopentane ring, a cyclohexane ring and the like.

Preferably, $R^1$ and $R^2$ are each a phenyl group, or $R^1$ and $R^2$ in combination show a tetramethylene group to form a cyclohexane ring together with the carbon atoms they are bonded to.

Examples of the aralkyl group for $R^3$ or $R^4$ include a group constituted with the above-mentioned aryl group and the above-mentioned alkyl group having 1 to 6 carbon atoms, such as a benzyl group, a 1-phenylethyl group, a 2-phenylethyl group, a 1-(1-naphthyl)ethyl group, a 1-(2-naphthyl)ethyl group, a 2-(1-naphthyl)ethyl group, a 2-(2-naphthyl)ethyl group, a 1-phenylpropyl group, a 2-phenylpropyl group, a 3-phenylpropyl group, a 1-phenylbutyl group, a 2-phenylbutyl group, a 3-phenylbutyl group, a 4-phenylbutyl group and the like.

Examples of the halogen atom, alkyl group having 1 to 6 carbon atoms, alkoxy group having 1 to 6 carbon atoms and haloalkoxy group having 1 to 6 carbon atoms for $R^3$ or $R^4$ are the same as the above-mentioned groups.

The haloalkyl group having 1 to 6 carbon atoms for $R^3$ or $R^4$ may be straight chain or branched chain, and examples thereof include a fluoromethyl group, a difluoromethyl group, a trifluoromethyl group, a 2-fluoroethyl group, a 2,2-difluoroethyl group, a 2,2,2-trifluoroethyl group, a 3-fluoropropyl group, a 4-fluorobutyl group, a 5-fluoropentyl group, a 6-fluorohexyl group and the like.

Examples of the alkyl group for $R^3$ or $R^4$ include an alkyl group having 1 to 10 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a 2-ethylbutyl group, a heptyl group, an octyl group, a nonyl group, a decyl group and the like.

Preferably, $R^3$ and $R^4$ are the same or different and each is a hydrogen atom or an alkyl group having 1 to 10 carbon atoms, more preferably, they are both hydrogen atoms or alkyl groups having 1 to 10 carbon atoms, still more preferably, they are both hydrogen atoms or methyl groups, particularly preferably, they are both methyl groups.

Specific examples of complex (1) include chiral iridium aqua complexes represented by the following formulas (2) to (4):
(2)
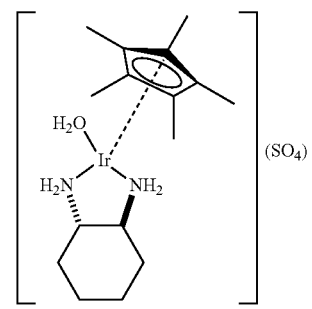
(3)
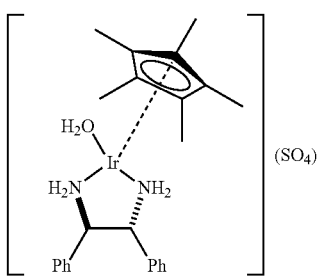
(4)
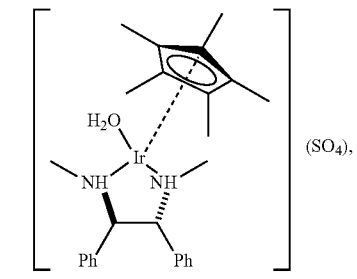
i.e., chiral iridium aqua complexes represented by the following formulas (2-S), (2-R), (3-R), (3-S), (4-R) and (4-S):
(2-S)
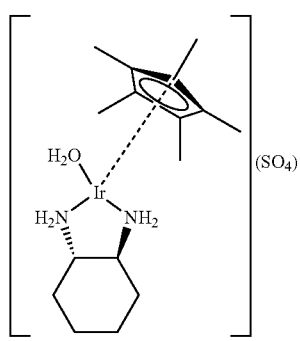
(2-R)
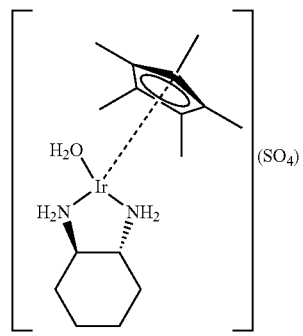
(3-S)
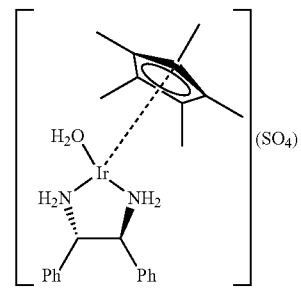
(3-R)
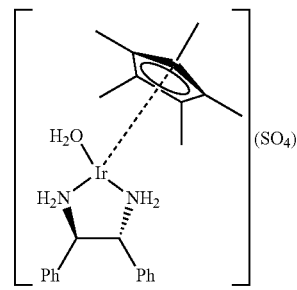
(4-S)
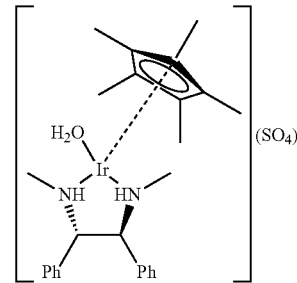
(4-R)
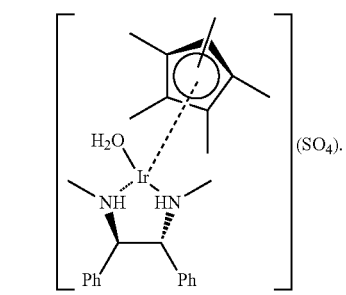
Of these, chiral iridium aqua complexes represented by the formulas (2-S), (3-R) and (4-R) are preferable.

Complex (1) can be produced by reacting an iridium complex represented by the formula (8):

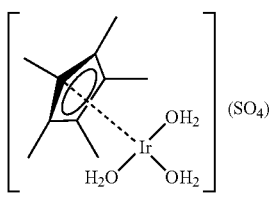

(hereinafter to be abbreviated as iridium complex (8)) with a chiral diamine represented by the formula (9):

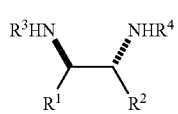

wherein $R^1$, $R^2$, $R^3$ and $R^4$ are as defined above (hereinafter to be abbreviated as diamine (9)).

Iridium complex (8) can be produced according to the method described in Organometallics 1999, 18, 5470-5474.

Specific examples of diamine (9) include chiral diamines represented by the following formulas:

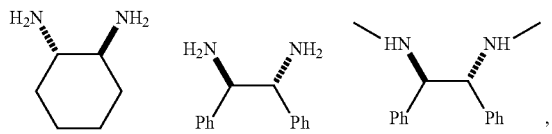

i.e., chiral diamines represented by the following formulas:

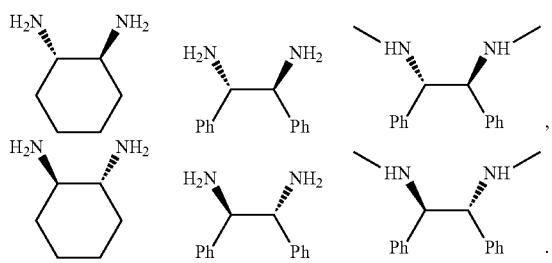

Diamine (9) may be commercially available or can be produced according to a known method.

The optical purity of diamine (9) is, nonlimitatively, more than 0% e.e. and not more than 100% e.e., preferably not less than 90% e.e., more preferably not less than 95% e.e.

The amount of diamine (9) to be used is generally 0.8 to 2 mol, preferably 0.9 to 1.2 mol from the aspects of economic efficiency, per 1 mol of iridium complex (8).

The reaction of iridium complex (8) with diamine (9) is generally carried out by mixing them in a solvent.

Examples of the solvent include water, alcohol solvents such as methanol and the like, mixed solvents thereof and the like. Of these, water, and a mixed solvent of water and an alcohol solvent are preferable. When a mixed solvent of water and an alcohol solvent is used, the volume ratio of water and the alcohol solvent is generally 1:1 to 10:1, preferably 1:1 to 5:1, though subject to change depending on the kind of diamine (9). The amount of the solvent to be used is generally 1- to 100-fold weight, relative to iridium complex (8).

The reaction temperature is generally 0 to 110° C., preferably 5 to 50° C. While the reaction time varies depending on the kind of diamine (9), it is generally 1 to 50 hr, preferably 1 to 24 hr.

Complex (1) can be isolated, for example, by concentrating the reaction mixture after completion of the reaction. The isolated complex (1) can be purified as necessary by a conventional purification means such as recrystallization and the like.

The obtained complex (1) shows good stability to air and water. In addition, solubility in water is also good.

Now, a chiral iridium aqua complex represented by the formula (5):

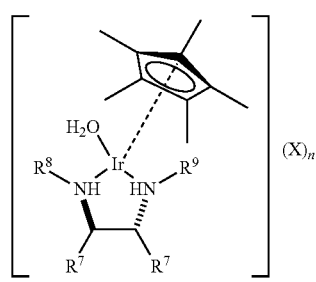

wherein
$R^7$ is an aryl group substituted by haloalkyl group(s) having 1 to 6 carbon atoms,
$R^8$ and $R^9$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom,
X is a monovalent or divalent anion, and
n is 2 when X is a monovalent anion, or n is 1 when X is a divalent anion (hereinafter to be abbreviated as complex (5)) is explained.

Examples of the aryl group for $R^7$ are the same as the above-mentioned groups. Of these, a phenyl group is preferable. Examples of the haloalkyl group having 1 to 6 carbon atoms for $R^7$ are the same as the above-mentioned groups. Of these, a trifluoromethyl group is preferable.

$R^7$ is preferably a phenyl group substituted by trifluoromethyl group(s), more preferably a 3-trifluoromethylphenyl group.

The aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, and alkyl group for $R^8$ or $R^9$ are the same groups as the examples of $R^3$ or $R^4$.

Preferably, $R^8$ and $R^9$ are the same or different and each is a hydrogen atom or an alkyl group having 1 to 10 carbon atoms, more preferably, they are both hydrogen atoms or alkyl groups having 1 to 10 carbon atoms, still more preferably, they are both hydrogen atoms or methyl groups, particularly preferably, they are both methyl groups.

Examples of the anion include a chloride ion, a bromide ion, an iodide ion, a methanesulfonate ion, a trifluoromethanesulfonate ion, a formate ion, an acetate ion, a trichloroacetate ion, a nitrate ion, a sulfate ion, an acetylacetonate ion, a hexafluorophosphate ion, a tetrafluoroborate ion and the like. Of these, a sulfate ion is preferable.

Examples of complex (5) include chiral iridium aqua complexes represented by the following formulas (5-R) and (5-S):

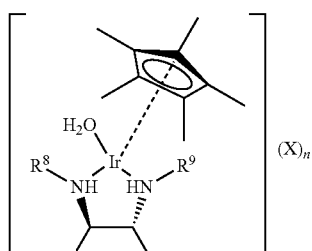

(5-R)

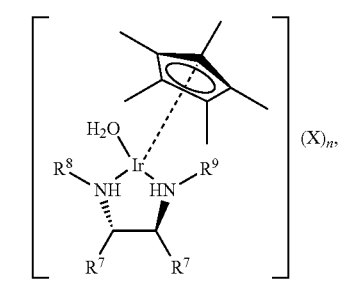

(5-S)

wherein $R^7$, $R^8$, $R^9$, X and n are as defined above. Complex (5) is preferably a chiral iridium aqua complex represented by the formula (5-R), more preferably a chiral iridium aqua complex represented by the following formula (12):

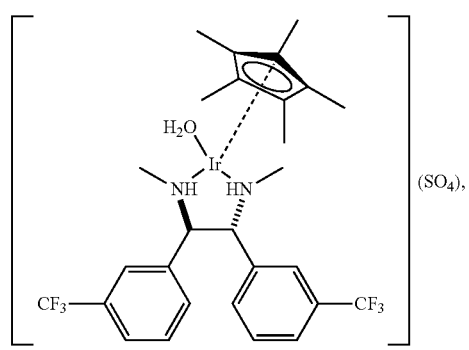

(12)

particularly preferably a chiral iridium aqua complex represented by the following formula (12-R):

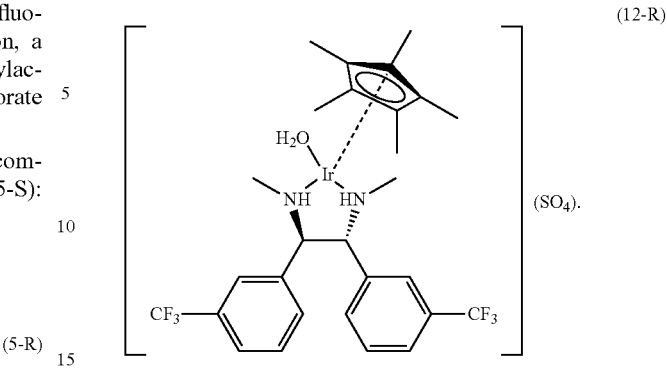

(12-R)

Complex (5) can be produced by reacting an iridium complex represented by the formula (10):

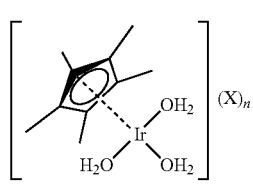

(10)

wherein X and n are as defined above (hereinafter to be abbreviated as iridium complex (10)) with a chiral diamine represented by the formula (11):

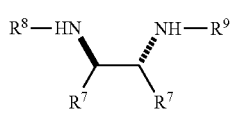

(11)

wherein $R^7$, $R^8$ and $R^9$ are as defined above (hereinafter to be abbreviated as diamine (11)).

Iridium complex (10) can be produced, for example, according to the method described in Organometallics 1999, 18, 5470-5474.

Examples of diamine (11) include a chiral diamine represented by the following formula:

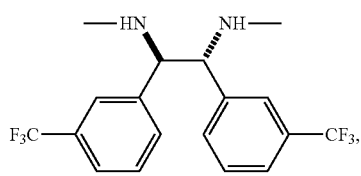

i.e., chiral diamines represented by

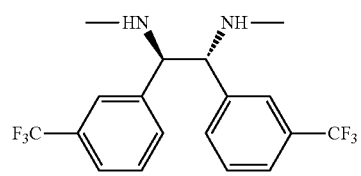

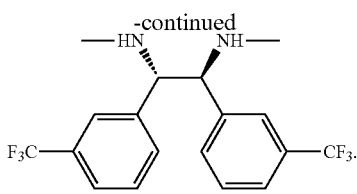

Diamine (11) may be commercially available or can be produced according to a known method.

The optical purity of diamine (11) is, nonlimitatively, more than 0% e.e. and not more than 100% e.e., preferably not less than 90% e.e., more preferably not less than 95% e.e.

The amount of diamine (11) to be used is generally 0.8 to 2 mol, preferably 0.9 to 1.2 mol from the aspects of economic efficiency, per 1 mol of iridium complex (10).

The reaction of iridium complex (10) with diamine (11) is generally carried out by mixing them in a solvent.

Examples of the solvent include water, alcohol solvents such as methanol, mixed solvents thereof and the like. Of these, water, and a mixed solvent of water and an alcohol solvent are preferable. When a mixed solvent of water and an alcohol solvent is used, the volume ratio of water and the alcohol solvent is generally 1:1 to 10:1, preferably 1:1 to 5:1, though subject to change depending on the kind of diamine (11). The amount of the solvent to be used is generally 1- to 100-fold weight, relative to iridium complex (10).

The reaction temperature is generally 0 to 110° C., preferably 5 to 50° C. While the reaction time varies depending on the kind of diamine (11), it is generally 1 to 50 hr, preferably 1 to 24 hr.

Complex (5) can be isolated, for example, by concentrating the reaction mixture after completion of the reaction. The isolated complex (5) can be purified as necessary by a conventional purification means such as recrystallization and the like.

The obtained complex (5) shows good stability to air and water. In addition, solubility in water is also good.

Now, the production method of an optically active hydroxy compound represented by the formula (7) (hereinafter to be abbreviated as optically active hydroxy compound (7)) by subjecting a carbonyl compound represented by the formula (6) (hereinafter to be abbreviated as carbonyl compound (6)) to asymmetric transfer hydrogenation in the presence of complex (1) or complex (5) is explained.

Examples of the halogen atom, alkyl group having 1 to 6 carbon atoms, haloalkyl group having 1 to 6 carbon atoms, alkoxy group having 1 to 6 carbon atoms, haloalkoxy group having 1 to 6 carbon atoms, aryl group and aralkyl group for $R^5$ are the same as the above-mentioned groups. The aryl group is preferably a phenyl group or a naphthyl group. Preferable examples of the substituent for the aryl group include a halogen atom, an alkyl group having 1 to 6 carbon atoms, an alkoxy group having 1 to 6 carbon atoms and a nitro group. Of these, a halogen atom, an alkyl group having 1 to 4 carbon atoms, an alkoxy group having 1 to 4 carbon atoms and a nitro group are more preferable.

Examples of the heteroaryl group for $R^5$ include a furyl group, a thienyl group, a pyridyl group, a benzofuranyl group, an indolyl group, a benzothiophenyl group, a pyrimidyl group, a pyrazinyl group, a quinolyl group, an isoquinolyl group, a phthalazinyl group, a quinazolinyl group, a quinoxalinyl group, a cinnolinyl group and the like, and a thienyl group is preferable.

Examples of the cycloalkyl group for $R^5$ include a cycloalkyl group having 3 to 8 carbon atoms. Of these, a cyclopropyl group, a cyclobutyl group, a cyclopentyl group, a cyclohexyl group, a cycloheptyl group, a cyclooctyl group and the like are preferable, and a cyclohexyl group is more preferable.

$R^5$ is preferably an aryl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; a heteroaryl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; or a cycloalkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, more preferably an aryl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; a heteroaryl group; or a cycloalkyl group, still more preferably a phenyl group; a phenyl group substituted by halogen atom(s); a phenyl group substituted by alkyl group(s) having 1 to 6 carbon atoms; a phenyl group substituted by alkoxy group(s) having 1 to 6 carbon atoms; a phenyl group substituted by nitro group(s); a naphthyl group; a thienyl group; or a cyclohexyl group, particularly preferably a phenyl group; a phenyl group substituted by halogen atom(s); a phenyl group substituted by alkyl group(s) having 1 to 6 carbon atoms; a phenyl group substituted by alkoxy group(s) having 1 to 6 carbon atoms; a phenyl group substituted by nitro group(s); or a naphthyl group.

Examples of the alkyl group having 1 to 6 carbon atoms for $R^6$ are the same as the above-mentioned groups. Specific examples of the carbamoyl group optionally substituted by one or two alkyl groups having 1 to 6 carbon atoms include a carbamoyl group, a methylcarbamoyl group, a morpholinocarbonyl group and the like.

Examples of the halogen atom, alkoxy group having 1 to 6 carbon atoms, haloalkoxy group having 1 to 6 carbon atoms and alkyl group for $R^6$ are the same as the above-mentioned groups.

$R^6$ is preferably an alkyl group having 1 to 10 carbon atoms optionally having at least one substituent selected from the group consisting of a halogen atom, an alkoxy group having 1 to 6 carbon atoms, a haloalkoxy group having 1 to 6 carbon atoms, a nitro group, a carboxyl group and a cyano group, or a carboxyl group, more preferably an alkyl group having 1 to 6 carbon atoms having at least one substituent selected from the group consisting of a carboxyl group, a nitro group and a cyano group, or a carboxyl group, particularly preferably a carboxymethyl group, a cyanomethyl group, a nitromethyl group or a carboxyl group.

Carbonyl compound (6) may be commercially available or can be produced according to a known method.

Carbonyl compound (6) is preferably a carbonyl compound represented by the following formula (6a):

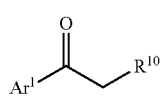

wherein
Ar$^1$ is a phenyl group optionally having at least one substituent selected from the group consisting of a halogen atom, an alkyl group having 1 to 6 carbon atoms, an alkoxy group having 1 to 6 carbon atoms and a nitro group; a naphthyl group; a thienyl group; or a cyclohexyl group, and
R$^{10}$ is a carboxyl group, a nitro group or a cyano group.

Complex (1) is preferably a chiral iridium aqua complex represented by any of the above-mentioned formulas (2) to (4). Complex (5) is preferably a chiral iridium aqua complex represented by the above-mentioned formula (12).

From the aspects of stereoselectivity in the asymmetric transfer hydrogenation, complex (5) is preferably used, and a chiral iridium aqua complex represented by the formula (5-R) is more preferably used. Moreover, complex (5) or a chiral iridium aqua complex represented by the formula (5-R), in each of which R$^7$ is a phenyl group substituted by trifluoromethyl group(s), is preferably used, and complex (5) or a chiral iridium aqua complex represented by the formula (5-R), in each of which R$^7$ is a 3-trifluoromethylphenyl group, is more preferably used.

In addition, complex (5) or a chiral iridium aqua complex represented by the formula (5-R), in each of which X is a sulfate ion, is preferably used, and complex (5) or a chiral iridium aqua complex represented by the formula (5-R), in each of which R$^7$ is a phenyl group substituted by trifluoromethyl group(s) and X is a sulfate ion, is more preferably used. Moreover, a chiral iridium aqua complex represented by the above-mentioned formula (12) or a chiral iridium aqua complex represented by the above-mentioned formula (12-R) is particularly preferably used.

The amount of complex (1) or complex (5) to be used is generally 0.001 to 0.1 mol, preferably 0.003 to 0.05 mol from the aspects of reactivity and economic efficiency, per 1 mol of carbonyl compound (6).

The asymmetric transfer hydrogenation of carbonyl compound (6) is generally carried out by mixing carbonyl compound (6), a hydrogen-donor compound and complex (1) or complex (5) in a solvent.

Examples of the hydrogen-donor compound include formic acid, formates such as sodium formate and the like, isopropanol and the like. Of these, from the aspects of conversion of carbonyl compound (6), formic acid and a salt thereof are preferable, and formic acid is more preferable. The amount of the hydrogen-donor compound to be used is generally 1 to 100 mol, preferably 2 to 10 mol from the aspects of economic efficiency, per 1 mol of carbonyl compound (6).

Examples of the solvent include water, alcohol solvents such as methanol and the like, and mixed solvents thereof and the like. Of these, water, and a mixed solvent of water and an alcohol solvent are preferable. When a mixed solvent of water and an alcohol solvent is used, the volume ratio of water and the alcohol solvent is generally 10:1 to 1:10, preferably 3:1 to 1:3, though subject to change depending on the kind and the amount of carbonyl compound (6) and complex (1) or (5). The amount of the solvent to be used is generally 1- to 100-fold weight, relative to carbonyl compound (6).

While the reaction temperature varies depending on the kind of carbonyl compound (6) and complex (1) or (5), it is generally 30 to 100° C., preferably 40 to 85° C. While the reaction time varies depending on the kind of complex (1) or (5), it is generally 1 to 50 hr, preferably 1 to 24 hr.

Optically active hydroxy compound (7) can be isolated, for example, by concentrating the reaction mixture after completion of the reaction. The isolated optically active hydroxy compound (7) can be purified by a conventional purification means such as recrystallization, extraction purification, distillation, adsorption treatment with activated carbon, silica, alumina and the like, chromatography method such as silica gel column chromatography and the like, and the like.

EXAMPLES

The present invention is explained more specifically in the following by referring to Examples, which are not to be construed as limitative. Cp* means η$^5$-pentamethylcyclopentadienyl anion.

Reference Example 1

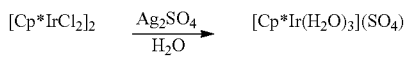

A mixture of water (12 mL), silver sulfate (1.05 g) and [Cp*IrCl$_2$]$_2$ (1.34 g) was stirred at room temperature for 12 hr. Then, the reaction mixture was filtered to remove silver chloride, and the solvent was evaporated under reduced pressure to give [Cp*Ir(H$_2$O)$_3$] (SO$_4$) (1.55 g) as a yellow solid. yield: 97%.

$^1$H NMR (300 MHz, D$_2$O) δ: 1.59 (s, 15H).

Reference Example 2

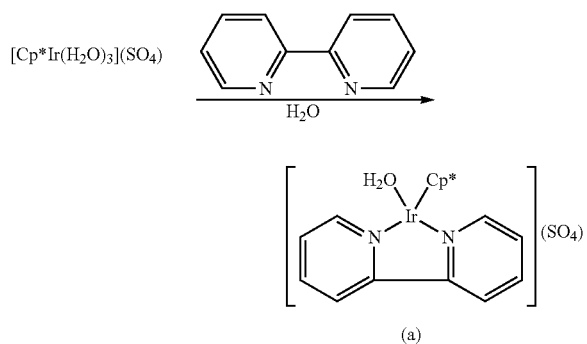

[Cp*Ir(H$_2$O)$_3$] (SO$_4$) (100 mg), bipyridine (34 mg) and water (1.5 mL) were mixed, and the mixture was stirred at room temperature for 12 hr. The solvent was evaporated under reduced pressure from the reaction mixture to quantitatively give an iridium aqua complex represented by the above-mentioned formula (a) as a yellow solid.

$^1$H NMR (300 MHz, D$_2$O) δ: 1.65 (s, 15H), 7.87 (t, J=5.7 Hz, 2H), 8.32 (t, J=8.1 Hz, 2H), 8.51 (d, J=8.1 Hz, 2H), 9.10 (d, J=5.7 Hz, 2H).

Example 1

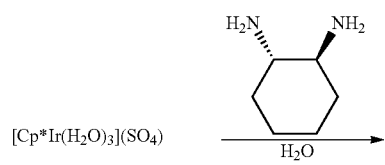

[Cp*Ir(H$_2$O)$_3$](SO$_4$) (100 mg), (1S,2S)-cyclohexane-1,2-diamine (25 mg) and water (2 ml) were mixed, and the mixture was stirred at room temperature for 7 hr. The solvent was evaporated under reduced pressure from the reaction mixture to give a chiral iridium aqua complex represented by the above-mentioned formula (2-S) as a green solid.

$^1$H NMR (300 MHz, MeOD) δ: 1.15-1.46 (m, 4H), 1.59-1.71 (m, 2H), 1.74 (s, 15H), 2.01-2.19 (m, 3H), 2.50-2.60 (m, 1H), 4.65-4.75 (m, 1H), 5.20-5.40 (m, 1H), 5.42-5.75 (m, 2H).

$^{13}$C NMR (75 MHz, MeOD) δ: 8.8, 25.6, 25.7, 33.7, 34.5, 58.7, 63.7, 86.1.

HR-MALDI calcd for C$_{16}$H$_{28}$IrN$_2$ [M-SO$_4$—H$_2$O—H]$^+$, 441.1882. Found 441.1876.

[α]$_D^{30}$ −44.24 (c 0.25, EtOH).

Example 2

[Cp*Ir(H$_2$O)$_3$](SO$_4$) (95 mg), (1R,2R)-1,2-diphenylethane-1,2-diamine (45 mg) and a mixed solvent (volume ratio=2:1, 3 mL) of water and methanol were mixed, and the obtained solution was stirred at room temperature for 12 hr. The solvent was evaporated under reduced pressure from the reaction mixture to give a chiral iridium aqua complex represented by the above-mentioned formula (3-R) as an orange solid.

$^1$H NMR (300 MHz, D$_2$O) δ: 1.75 (s, 15H), 4.18 (br s, 2H), 7.20-7.28 (m, 10H).

$^1$H NMR (300 MHz, MeOD) δ: 1.81 (s, 15H), 3.90-4.00 (m, 1H), 4.28-4.38 (m, 1H), 7.14-7.41 (m, 10H).

$^{13}$C NMR (75 MHz, MeOD) δ: 8.9, 63.7, 68.3, 86.5, 128.7, 129.0, 129.1, 129.3, 137.9, 138.9.

HR-MALDI calcd for C$_{24}$H$_{30}$IrN$_2$ [M-SO$_4$—H$_2$O—H]$^+$, 539.2038. Found 539.1827.

[α]$_D^{30}$ +70.43 (c 0.45, CHCl$_3$).

Example 3

[Cp*Ir(H$_2$O)$_3$](SO$_4$) (26.0 mg), (1R,2R)—N,N'-dimethyl-1,2-diphenylethane-1,2-diamine (14 mg) and a mixed solvent (volume ratio=2:1, 1.2 mL) of water and methanol were mixed, and the obtained solution was stirred at room temperature for 24 hr. The solvent was evaporated under reduced pressure from the reaction mixture to give a chiral iridium aqua complex represented by the above-mentioned formula (4-R) as a brown solid.

$^1$H NMR (300 MHz, MeOD) δ: 1.75 (s, 15H), 2.68 (s, 3H), 2.91 (s, 3H), 3.85 (d, J=12.3 Hz, 1H), 4.08 (d, J=12.3 Hz, 1H), 7.15-7.29 (m, 10H).

$^{13}$C NMR (75 MHz, MeOD) δ: 8.9, 37.1, 41.5, 72.6, 76.8, 87.7, 129.3, 129.5, 129.9, 135.0, 136.1.

HR-MALDI calcd for $C_{26}H_{34}IrN_2$ [M-SO$_4$—H$_2$O—H]$^+$ 567.2347. found 567.2338.

$[\alpha]_D^{24}$+75.48 (c 0.43, EtOH).

Example 4

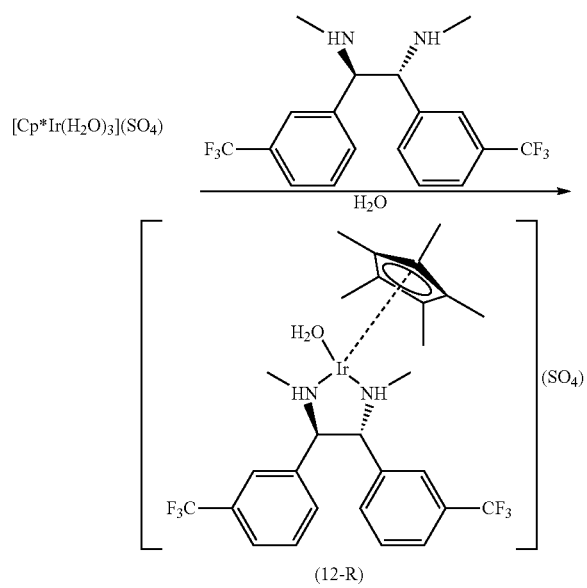

[Cp*Ir(H$_2$O)$_3$] (SO$_4$) (95 mg), (1R,2R)—N,N'-dimethyl-1,2-bis[3-(trifluoromethyl)phenyl]ethane-1,2-diamine (79 mg) and a mixed solvent (volume ratio=2:1, 6 mL) of water and methanol were mixed, and the obtained solution was stirred at room temperature for 12 hr. The solvent was evaporated under reduced pressure from the reaction mixture to give a chiral iridium aqua complex represented by the above-mentioned formula (12-R) as a yellow solid.

$^1$H NMR (300 MHz, MeOD) δ: 1.74 (s, 15H), 2.70 (s, 3H), 2.94 (s, 3H), 4.05 (d, J=11.9 Hz, 1H), 4.27 (d, J=11.9 Hz, 1H), 7.45-7.80 (m, 8H).

$^{13}$C NMR (75 MHz, MeOD) δ: 9.1, 37.4, 41.8, 71.9, 75.8, 87.9, 123.7 (c, J=279.9 Hz), 123.7 (c, J=270.0 Hz), 126.2 (c, J=3.7 Hz), 126.5 (c, J=3.6 Hz), 130.1, 130.8, 131.8, 131.3 (c, J=32 Hz), 135.9, 137.3.

HR-MALDI calcd for $C_{28}H_{32}F_6IrN_2$ [M-SO$_4$—H$_2$O—H]$^+$ 703.2099. found 703.2103.

$[\alpha]_D^{27}$+57.45 (c 0.50, EtOH).

Example 5

A mixed solvent (volume ratio=1:1, 5 mL) of water and methanol and the iridium aqua complex shown in the following Table 1 (0.5 mol % relative to 2-cyanoacetophenone) were mixed, and 2-cyanoacetophenone (1 mmol) and the hydrogen-donor compound shown in the following Table 1 (5 mmol) were added to the obtained solution at room temperature. The obtained mixture was stirred at 70° C. After confirming the disappearance of 2-cyanoacetophenone by thin layer chromatography, the reaction was quenched with brine (20 mL). The reaction mixture was subjected to extraction treatment (three times) with ethyl acetate (20 mL), and the obtained organic layers were combined. The combined organic layer was dried over anhydrous sodium sulfate, and concentrated. The obtained residue was purified by silica gel column chromatography (eluent: dichloromethane:methanol=20:1) to give (S)-3-phenyl-3-hydroxypropionitrile. The conversion and optical purity are shown in Table 1.

TABLE 1

| No. | Iridium Aqua Complex | Hydrogen-Donor Compound | Conversion % | Optical Purity (% e. e.) |
|---|---|---|---|---|
| 5-1 | 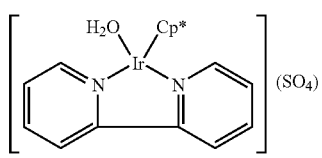 | HCO$_2$Na | 87 | — |
| 5-2 | 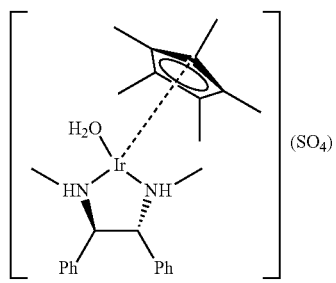 | HCO$_2$Na | 63 | 83 |

TABLE 1-continued

| No. | Iridium Aqua Complex | Hydrogen-Donor Compound | Conversion % | Optical Purity (% e. e.) |
|---|---|---|---|---|
| 5-3 | [Ir complex with H₂O, Cp*, diamine with 3-CF₃ phenyl groups] (SO₄) | HCO₂Na | 84 | 95 |
| 5-4 | [Ir complex with H₂O, Cp*, diamine with 3-CF₃ phenyl groups] (SO₄) | HCO₂H | 99 | 95 |

Example 6

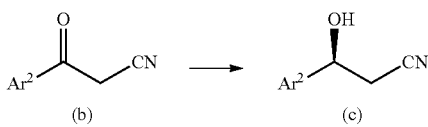

A mixed solvent (volume ratio=1:1, 5 mL) of water and methanol and a chiral iridium aqua complex represented by the formula (12-R) (0.5 mol % relative to a compound represented by the formula (b)) were mixed, and a compound represented by the formula (b) shown in Table 2 (1 mmol) and formic acid (5 mmol) were added to the obtained solution at room temperature. The obtained mixture was stirred at 70° C. to carry out asymmetric transfer hydrogenation. After confirming the disappearance of the compound represented by the formula (b) by thin layer chromatography, the reaction was quenched with brine (20 mL). The reaction mixture was subjected to extraction treatment (three times) with ethyl acetate (20 mL), and the obtained organic layers were combined. The combined organic layer was dried over anhydrous sodium sulfate, and concentrated. The obtained residue was purified by silica gel column chromatography (eluent: dichloromethane:methanol=20:1) to give the corresponding optically active hydroxy compound represented by the formula (c). The configurations of the obtained optically active hydroxy compounds were all S-configurations. The reaction time, yield and optical purity are shown in Table 2.

TABLE 2

| No. | Ar² | Reaction Time (Hr) | Yield (%) | Optical Purity (% e. e.) |
|---|---|---|---|---|
| 6-1 | phenyl | 12 | 96 | 95 |
| 6-2 | 2-methylphenyl | 24 | 92 | 99 |
| 6-3 | 4-methylphenyl | 18 | 93 | 92 |
| 6-4 | 2-methoxyphenyl | 10 | 90 | 99 |
| 6-5 | 3-methoxyphenyl | 15 | 91 | 97 |

TABLE 2-continued

| No. | Ar² | Reaction Time (Hr) | Yield (%) | Optical Purity (% e.e.) |
|---|---|---|---|---|
| 6-6 | H₃CO—C₆H₄— | 20 | 90 | 90 |
| 6-7 | 2-I-C₆H₄— | 44 | 45 | 99 |
| 6-8 | Br—C₆H₄— | 18 | 87 | 90 |
| 6-9 | F—C₆H₄— | 12 | 85 | 87 |
| 6-10 | 3-O₂N-C₆H₄— | 12 | 96 | 87 |
| 6-11 | 2-naphthyl | 15 | 88 | 95 |

Example 7

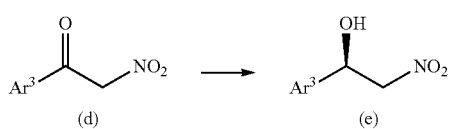

A mixed solvent (volume ratio=1:1, 5 mL) of water and methanol and a chiral iridium aqua complex represented by the formula (12-R) (0.5 mol % relative to a compound represented by the formula (d)) were mixed, and a compound represented by the formula (d) shown in Table 3 (1 mmol) and formic acid (5 mmol) were added to the obtained solution at room temperature. The obtained mixture was stirred at 70° C. to carry out asymmetric transfer hydrogenation. After confirming the disappearance of the compound represented by the formula (d) by thin layer chromatography, the reaction was quenched with brine (20 ml). The reaction mixture was subjected to extraction treatment (three times) with ethyl acetate (20 mL), and the obtained organic layers were combined. The combined organic layer was dried over anhydrous sodium sulfate, and concentrated. The obtained residue was purified by silica gel column chromatography (eluent: dichloromethane:methanol=20:1) to give the corresponding optically active hydroxy compound represented by the formula (e). The configurations of the obtained optically active hydroxy compounds were all R-configurations. The reaction time, yield and optical purity are shown in Table 3.

TABLE 3

| No. | Ar³ | Reaction Time (Hr) | Yield (%) | Optical Purity (% e.e.) |
|---|---|---|---|---|
| 7-1 | C₆H₅— | 5 | 85 | 95 |
| 7-2 | 2-CH₃-C₆H₄— | 18 | 51 | 99 |
| 7-3 | tert-C₄H₉—C₆H₄— | 8 | 77 | 92 |
| 7-4 | 2-OCH₃-C₆H₄— | 12 | 75 | 98 |
| 7-5 | 3-Br-C₆H₄— | 15 | 35 | 94 |
| 7-6 | 2-naphthyl | 10 | 78 | 93 |

Example 8

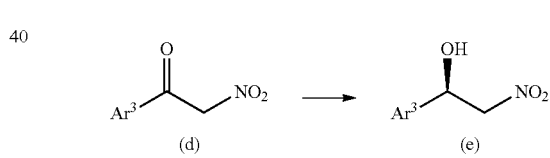

A mixed solvent (volume ratio=1:1, 5 mL) of water and formic acid and a chiral iridium aqua complex represented by the formula (12-R) (0.5 mol % relative to a compound represented by the formula (d)) were mixed, and a compound represented by the formula (d) shown in Table 4 (1 mmol) was added to the obtained solution at room temperature. The obtained mixture was stirred at 70° C. to carry out asymmetric transfer hydrogenation. After confirming the disappearance of the compound represented by the formula (d) by thin layer chromatography, the reaction was quenched with brine (20 mL). The reaction mixture was subjected to extraction treatment (three times) with ethyl acetate (20 mL), and the obtained organic layers were combined. The combined organic layer was dried over anhydrous sodium sulfate, and concentrated. The obtained residue was purified by silica gel column chromatography (eluent: dichloromethane:methanol=20:1) to give the corresponding optically active hydroxy compound represented by the formula (e). The configurations of the obtained optically active hydroxy compounds were all R-configurations. The reaction time, yield and optical purity are shown in Table 4.

TABLE 4

| No. | Ar³ | Reaction Time (Hr) | Yield (%) | Optical Purity (% e.e.) |
|---|---|---|---|---|
| 8-1 | 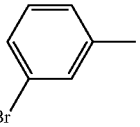 | 3 | 78 | 93 |
| 8-2 | 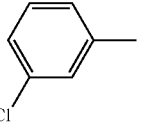 | 2 | 81 | 92 |

Example 9

A mixed solvent (volume ratio=1:1, 5 mL) of water and formic acid and a chiral iridium aqua complex represented by the formula (12-R) (0.5 mol % relative to 2-methylphenylglyoxylic acid) were mixed, and 2-methylphenylglyoxylic acid (1 mmol) was added to the obtained solution at room temperature. The obtained mixture was stirred at room temperature to carry out asymmetric transfer hydrogenation. After confirming the disappearance of 2-methylphenylglyoxylic acid by thin layer chromatography, the reaction was quenched with brine (20 mL). The reaction mixture was subjected to extraction treatment (three times) with ethyl acetate (20 mL), and the obtained organic layers were combined. The combined organic layer was dried over anhydrous sodium sulfate, and concentrated. The obtained residue was purified by silica gel column chromatography (eluent: dichloromethane:methanol=20:1) to give the corresponding (R)-2-(2-methylphenyl)-2-hydroxyacetic acid. Yield 95%, optical purity 83% e.e.

INDUSTRIAL APPLICABILITY

The chiral iridium aqua complex represented by the formula (1) or the formula (5) of the present invention is a novel complex, and it has good stability to air and water and high solubility in water. Therefore, the complex can be used for the reaction in water or in a hydrophilic solvent which are environmentally friendly and suitable for green chemistry. The chiral iridium aqua complex represented by the formula (1) or the formula (5) is particularly preferably used for asymmetric transfer hydrogenation of a carbonyl compound, and can produce an optically active hydroxy compound in a high yield with good stereoselectivity.

The invention claimed is:

1. A chiral iridium aqua complex represented by the formula (5):

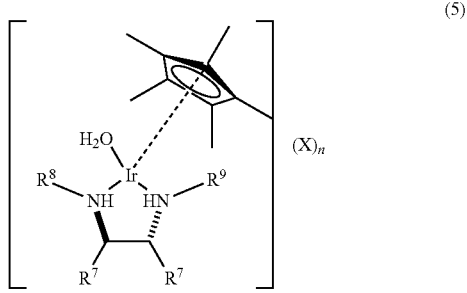

(5)

wherein
$R^7$ is an aryl group substituted by haloalkyl group(s) having 1 to 6 carbon atoms, $R^8$ and $R^9$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, X is a monovalent or divalent anion, and n is 2 when X is a monovalent anion, or n is 1 when X is a divalent anion.

2. The complex of claim 1, wherein the chiral iridium aqua complex represented by the formula (5) is a complex represented by the formula (5-R):

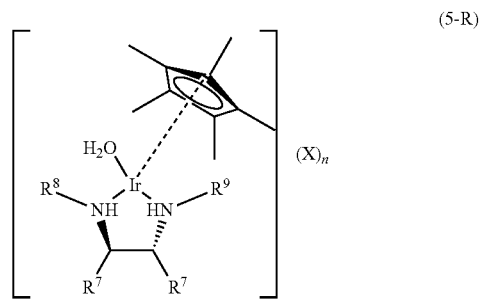

(5-R)

wherein $R^7$, $R^8$, $R^9$, X and n are as defined in claim 1.

3. The complex of claim 1, wherein the aryl group substituted by haloalkyl group(s) having 1 to 6 carbon atoms is a phenyl group substituted by trifluoromethyl group(s).

4. The complex of claim 3, wherein the phenyl group substituted by trifluoromethyl group(s) is a 3-trifluoromethylphenyl group.

5. The complex of claim 3, wherein $R^8$ and $R^9$ are the same or different and each is a hydrogen atom or an alkyl group having 1 to 10 carbon atoms.

6. The complex of claim 1, wherein X is a chloride ion, a bromide ion, an iodide ion, a methanesulfonate ion, a trifluoromethanesulfonate ion, a formate ion, an acetate ion, a trichloroacetate ion, a nitrate ion, a sulfate ion, an acetylacetonate ion, a hexafluorophosphate ion or a tetrafluoroborate ion.

7. The complex of claim 1, wherein X is a sulfate ion.

8. A method of producing a chiral iridium aqua complex represented by the formula (5):

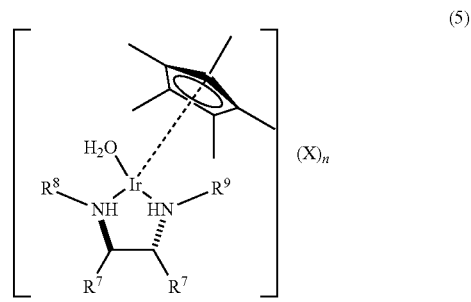

(5)

wherein
$R^7$ is an aryl group substituted by haloalkyl group(s) having 1 to 6 carbon atoms,
$R^8$ and $R^9$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, X is a monovalent or divalent anion, and n is 2 when X is a monovalent anion, or n is 1 when X is a divalent anion, which comprises reacting an iridium complex represented by the formula (10):

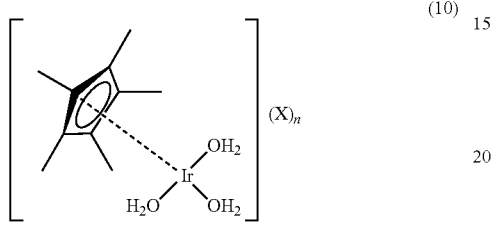

(10)

wherein X and n are as defined above,
with a chiral diamine represented by the formula (11):

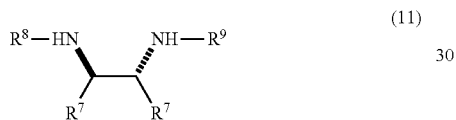

(11)

wherein $R^7$, $R^8$ and $R^9$ are as defined above.

9. A method of producing an optically active hydroxy compound represented by the formula (7):

(7)

wherein $R^5$ is an aryl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; a heteroaryl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; a cycloalkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group; or an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, $R^6$ is a carbamoyl group optionally substituted by one or two alkyl groups having 1 to 6 carbon atoms wherein the two alkyl groups having 1 to 6 carbon atoms in combination optionally form a ring containing the nitrogen atom, and the methylene group of the ring is optionally replaced by an oxygen atom; an alkyl group optionally having at least one substituent selected from the group consisting of a halogen atom, an alkoxy group having 1 to 6 carbon atoms, a haloalkoxy group having 1 to 6 carbon atoms, a nitro group, a carboxyl group and a cyano group; or a carboxyl group, and the carbon atom marked with * is an asymmetric carbon atom, which comprises subjecting a carbonyl compound represented by the formula (6):

(6)

wherein $R^5$ and $R^6$ are as defined above, to asymmetric transfer hydrogenation in the presence of a chiral iridium aqua complex represented by the formula (5):

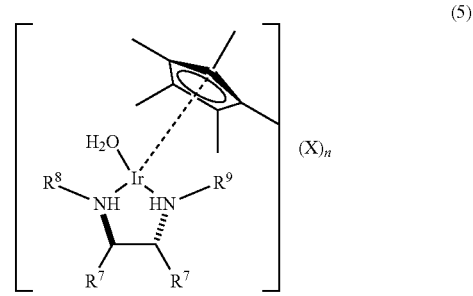

(5)

wherein $R^7$ is an aryl group substituted by haloalkyl group(s) having 1 to 6 carbon atoms, $R^8$ and $R^9$ are the same or different and each is an aralkyl group optionally having at least one substituent selected from the group consisting of a halogen atom, an alkyl group having 1 to 6 carbon atoms, a haloalkyl group having 1 to 6 carbon atoms, an alkoxy group having 1 to 6 carbon atoms, a haloalkoxy group having 1 to 6 carbon atoms, a nitro group, a carboxyl group and a cyano group, or an alkyl group or a hydrogen atom, X is a monovalent or divalent anion, and n is 2 when X is a monovalent anion, or n is 1 when X is a divalent anion.

10. The method of claim 9, wherein the asymmetric transfer hydrogenation is carried out in the presence of formic acid or a salt thereof.

11. The method of claim 9, wherein the asymmetric transfer hydrogenation is carried out in the presence of formic acid.

12. The method of claim 9, wherein the asymmetric transfer hydrogenation is carried in water or in a mixed solvent of water and an alcohol solvent.

13. The method of claim 9, wherein $R^6$ is a carboxyl group, a carboxymethyl group, a cyanomethyl group or a nitromethyl group.

* * * * *